United States Patent [19]

Richter et al.

[11] Patent Number: 5,758,766
[45] Date of Patent: Jun. 2, 1998

[54] CONTAINER WITH MULTIPLE CHAMBERS, TO PACKAGE COMPONENTS SEPARATELY PRIOR TO USE IN ADMIXTURE

[75] Inventors: Hans-Uwe Richter, Wuppertal, Germany; Marcel Aeby, Basle, Switzerland; Willy Baettig, Pratteln, Switzerland; Karl Meyer, Rheinfelden, Switzerland

[73] Assignee: Novartis Corporation, Summit, N.J.

[21] Appl. No.: 556,929

[22] PCT Filed: May 19, 1994

[86] PCT No.: PCT/EP94/01614

§ 371 Date: Mar. 28, 1996

§ 102(e) Date: Mar. 28, 1996

[87] PCT Pub. No.: WO94/27886

PCT Pub. Date: Dec. 8, 1994

[30] Foreign Application Priority Data

Jun. 2, 1993 [DE] Germany .................. 43 18 312.3

[51] Int. Cl.$^6$ ............................................. B65D 77/00
[52] U.S. Cl. .................. 206/216; 206/256; 206/271; 229/120.18; 229/120.011
[58] Field of Search ............................... 206/216, 256, 206/265, 271, 273; 229/120.18, 120.03, 120.01, 120.011; 220/462, 416

[56] References Cited

U.S. PATENT DOCUMENTS

| | | | |
|---|---|---|---|
| 1,630,497 | 5/1927 | Morris | 229/120.01 |
| 2,327,529 | 8/1943 | Kieckhefer et al. | 229/120.011 |
| 3,051,367 | 8/1962 | Einhorn | 220/462 |
| 3,253,765 | 5/1966 | Train | 229/120.01 |
| 3,567,105 | 3/1971 | McFarlin | 206/216 |
| 3,576,290 | 4/1971 | Marchisen | 220/462 |
| 3,578,234 | 5/1971 | Marchisen | 220/462 |
| 3,731,870 | 5/1973 | Buttery | 229/120.03 |
| 3,957,195 | 5/1976 | Lin | 220/462 |
| 4,099,665 | 7/1978 | Bergstein | 220/403 |
| 4,105,154 | 8/1978 | Meyers et al. | 229/120.18 |
| 4,179,061 | 12/1979 | Gilbert | 229/120.18 |
| 4,250,993 | 2/1981 | Roccaforte et al. | 206/216 |
| 4,293,091 | 10/1981 | Gerard | 229/120.18 |
| 4,333,569 | 6/1982 | Hammacher | 229/120.01 |
| 5,174,444 | 12/1992 | Adams et al. | 229/120.011 |
| 5,413,276 | 5/1995 | Sheffer | 229/120.03 |

FOREIGN PATENT DOCUMENTS

| | | | |
|---|---|---|---|
| 551634 | 10/1956 | Belgium | 206/47 R |
| 551635 | 10/1956 | Belgium | 383/7 |
| 0190385 | 8/1986 | European Pat. Off. | |
| A083511 | 7/1964 | France | 229/120.18 |
| 2696995 | 4/1994 | France | |
| 1162271 | 1/1964 | Germany | |
| 7230857 | 8/1972 | Germany | |
| 2127442 | 12/1972 | Germany | |
| 8312584 | 9/1983 | Germany | |
| 8715350 | 2/1988 | Germany | |
| 1038492 | 8/1956 | United Kingdom | |
| 1251567 | 10/1969 | United Kingdom | |
| 8808602 | 11/1988 | WIPO | |
| 9116246 | 10/1991 | WIPO | |
| WO 91/16246 | 10/1991 | WIPO | 229/120.18 |

OTHER PUBLICATIONS

Derwent Abstract 84–276281 (of DE 8312584.1).
Derwent Abstract 94–153359/19 (of FR 2,696995).
Derwent Abstract 86–213294 (of EP 0190385).

*Primary Examiner*—Paul T. Sewell
*Assistant Examiner*—Nhan T. Lam
*Attorney, Agent, or Firm*—William A. Teoli, Jr.; John D. Peabody, III

[57] ABSTRACT

The invention provides a package for accommodating product having at least two components, which package has at least two self-contained chambers in which the individual components of the product can be stored in such a manner that they are hermetically separated from one another. The end regions of the chamber walls are in the form of a common closure for the individual chambers such the individual chambers can only be opened simultaneously.

13 Claims, 5 Drawing Sheets

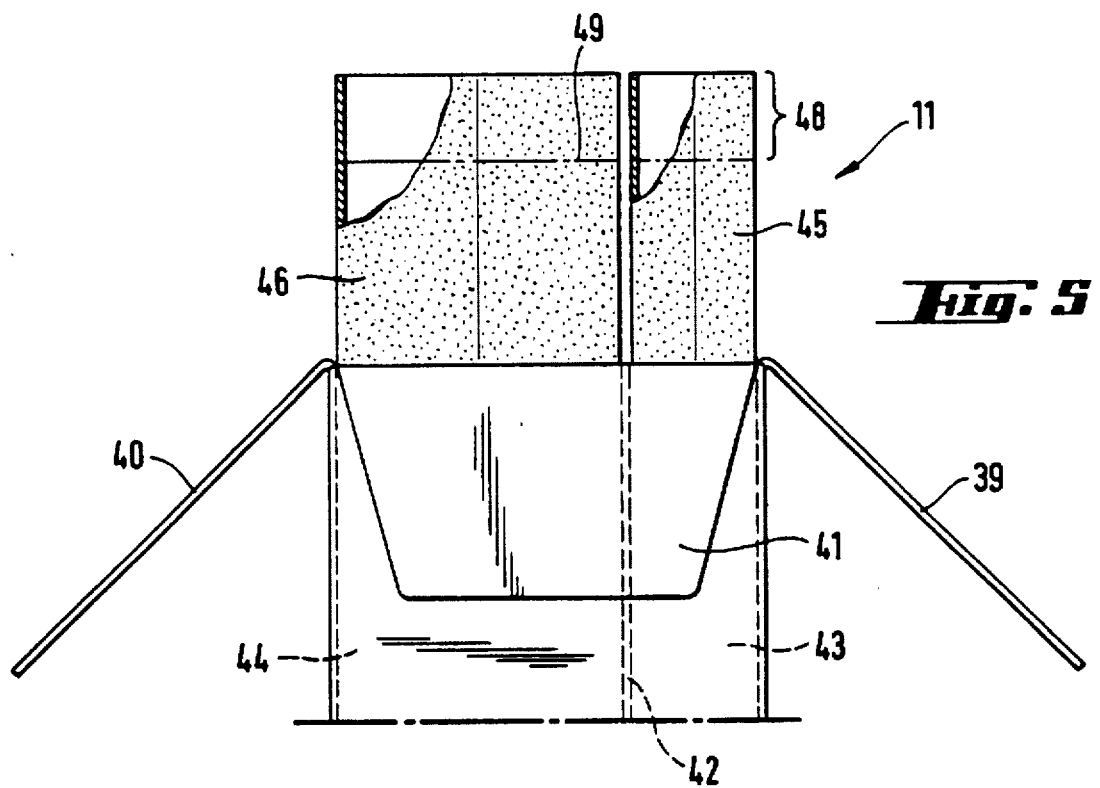
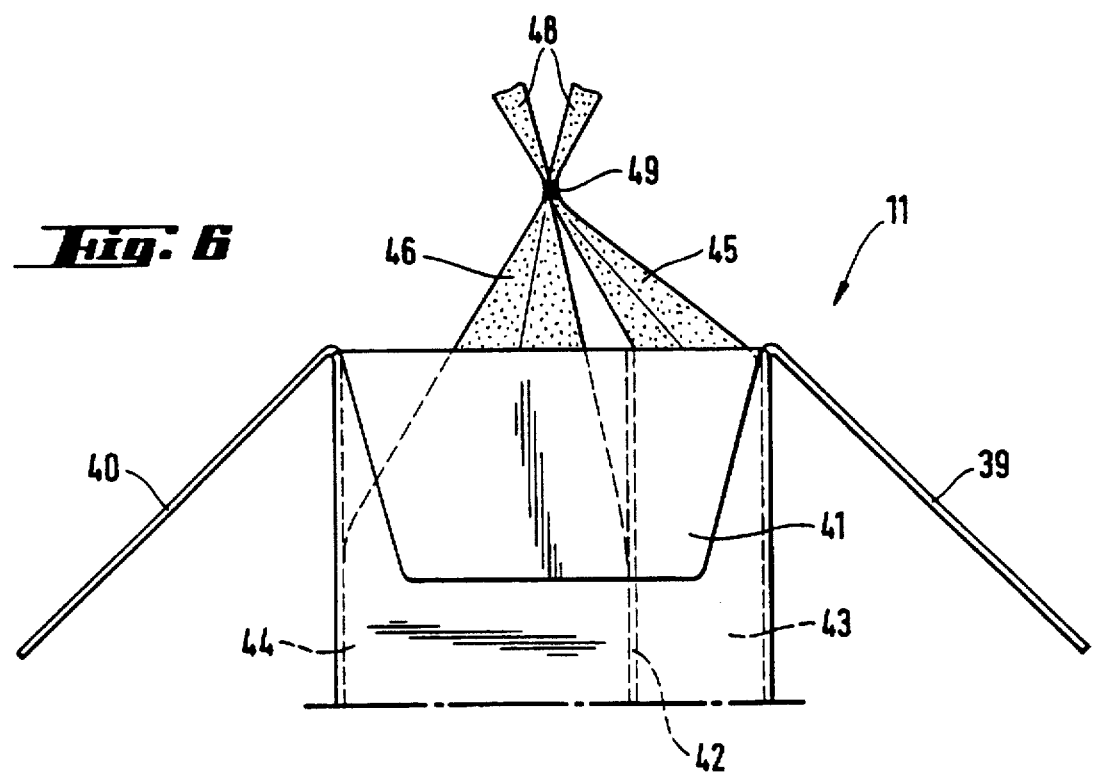

CONTAINER WITH MULTIPLE CHAMBERS, TO PACKAGE COMPONENTS SEPARATELY PRIOR TO USE IN ADMIXTURE

The invention relates to a package for accommodating a product having at least two components according to the preamble of patent claim 1. The invention relates also to a method of removing such a product from a package according to the preamble of patent claim 19.

German Utility Model No. 83 12 584.1 discloses a package in which an inner sachet package is provided for the packaging of two or more different chemicals that react with one another. A known package of that type is used, for example, to store a product, consisting of different substances that are not to be mixed together until they are to be used, inside a package in such a manner that the individual substances are completely separate from one another. In that package, there are arranged inside an inner sachet at least two further sachets which accommodate the different chemicals.

That package, which is advantageous per se, has the disadvantage that it is not convenient to handle when the product is used. In addition to the outer folded carton, the user also has to open each of the individual envelopes, which contain very different substances, and it is virtually impossible to remove both substances simultaneously.

The problem underlying the invention is therefore to provide a package for a product consisting of at least two components in which the individual components are hermetically separated from one another, and which is easy to handle when using the product.

A further problem underlying the invention is to provide a method of removing a product having at least two components from a package, in which method the individual components can only be emptied out of the package simultaneously and are brought into contact with one another for the first time only when they are being removed from the package.

The above problems are solved on the one hand by a package having the characterising features of patent claim 1 and on the other by a method comprising the steps listed in the second part of patent claim 19. The dependent patent claims relate to especially preferred forms of the invention.

The invention provides especially a package for accommodating a product having at least two components, which package has at least two self-contained chambers in which the individual components of the product can be stored in such a manner that they are hermetically separated from one another. The individual chambers are connected together in such a manner that they can be separated from one another only by destroying at least one chamber wall. The end regions of the chamber walls are in the form of a common closure for the individual chambers such that the individual chambers can only be opened simultaneously.

In an especially preferred form of the invention, the package is in the form of a folded carton in which there are arranged in a fixed manner inside the folded carton at least two inner sachets each of which accommodates one of the components directly; when the inner sachets have been filled separately with the components, the top end regions thereof that project out of the inside of the folded carton form a common closure.

The common closure according to the invention of the two inner sachets arranged inside the folded carton enables the user to use the product directly in a simple manner by emptying the folded carton after opening the closure of the two inner sachets. The two components are thus brought into contact with one another and mixed together only during the emptying operation. Therefore, during the storage and transportation of the individual components of the product inside the inner sachets, it is not possible for the components to interact with one another. In addition, when the common closure has been opened, the product can be used immediately by emptying the package, the individual components mixing together substantially uniformly at the same time.

In one embodiment of the invention, the folded carton also has two chambers, separated by a dividing wall, in which the inner sachets are arranged. That embodiment has the additional advantage that the two components, which must not come into contact with one another before being used, are additionally separated from one another by a further barrier, with the result that the safety during transportation is even greater.

Advantageously, it is also possible to use the dividing wall to divide the useful volume of the folded carton into chambers of different sizes, which, naturally, contain inner sachets that are also of different sizes. Provided that the inner sachets are filled to matching levels and that the particle sizes are identical, it is then possible to achieve approximately a particular mixing ratio when emptying the carton.

In a further embodiment of the invention, the front, dividing and back walls each have an integrally arranged top flap; the length of the top flaps of the back wall and the dividing wall corresponds substantially to the distance of the wall in question from the front wall; end regions of the inner sachets project beyond the top flaps of the back wall and the dividing wall, which flaps can be folded over in the direction towards the front wall; the end regions form a common closure when the top flaps of the back wall and the dividing wall have been folded over, and when the top flap of the front wall is folded over in the opposite direction the closure is held inside the contour of the folded canon.

That embodiment of the invention provides a common closure for the two inner sachets that is simple to produce as well as to open, the top flaps and the end regions of the inner sachets arranged thereon cooperating in an advantageous manner. In addition, the closure of the inner sachets is arranged between the top flaps of the back and front walls in such a manner that it is protected.

Furthermore, in that embodiment the package can be opened in an advantageously simple manner, for example using scissors to cut off the end regions of the inner sachets, which end regions project when the outer top flap has been opened.

In principle, it is possible in accordance with a further embodiment for the folded carton to consist of two folded carton portions, each forming a chamber, which are connected to one another to form a double-thickness dividing wall.

That form of the subject of the invention has, firstly, the advantage that the dividing wall is of double-walled construction, thus improving further the separation of the individual components from one another. Secondly, that form of the folded carton makes it possible in principle for the user to store, for example, individual components of a product or different products sold together, in different places in the folded carton portions once they have been detached from each other when the carton has been opened.

In a preferred embodiment there are arranged on both sides of the package blank, between the back wall and the dividing wall, gusset flaps that can be folded in in the direction towards the top flap of the front wall and the inside of the folded carton.

That additional arrangement of the gusset flaps improves the folding-over of the top flaps and the lateral folding-in of the inner sachets in such a manner that a neat, visually appealing top region of the folded carton is produced, the lateral gusset flaps also providing a certain amount of protection for the inner sachets.

In order further to improve the production of the common closure for the inner sachets and to improve the closing of the folded carton, at least portions of the inner sachets may additionally be secured by means of adhesive to the back wall and the dividing wall, to the associated top flaps and to the gusset flaps.

In an embodiment that is ultimately especially preferred, the common closure is in the form of a heat-sealed or glued seam. That type of common closure for the two inner sachets is not only simple to produce and simple to open by cutting through the inner sachets below the seam, but also guarantees that the individual components in the inner sachets are hermetically sealed off.

Other advantages of the invention will be apparent from the dependent patent claims which follow and from the description of the embodiments given by way of example.

FIG. 5 is a folded carton having inner sachets which project at the top, and

FIG. 6 is a folded carton according to FIG. 5 having a common closure for the inner sachets.

Figure 1:
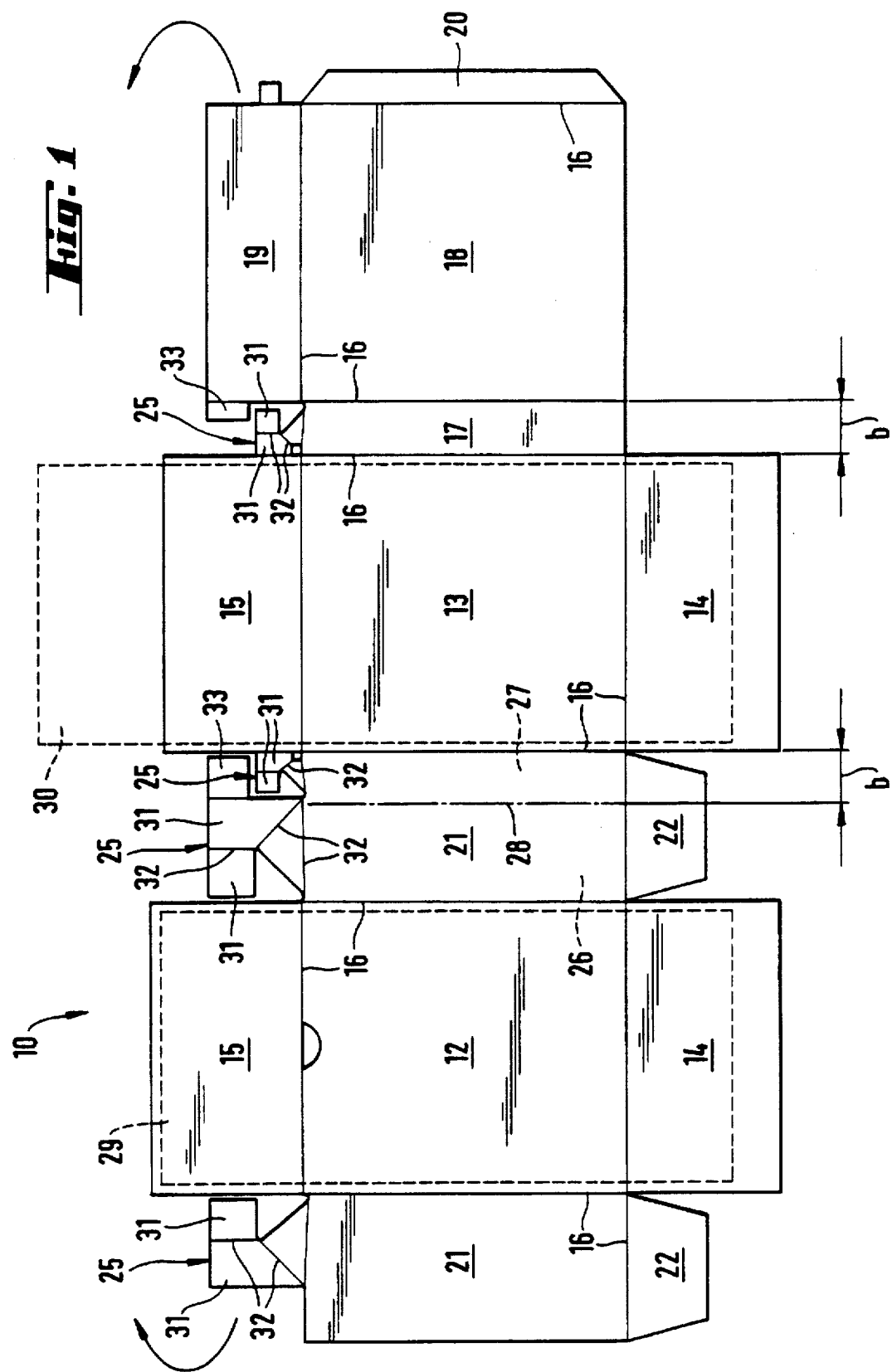
FIG. 1 is a plan view of a package blank.

In the drawings, a package blank that when assembled forms a folded carton 11 has the reference numeral 10.

The package blank 10 has firstly a front wall 12 and a back wall 13 on which bottom flaps 14 are integrally arranged at the bottom and top flaps 15 are integrally arranged at the top, fold lines 16 being provided in the transitional region from the front and back walls 12, 13 to the bottom and top flaps 14, 15. Via a connecting strip 17, there is arranged on the back wall 13 a dividing wall 18 that is provided on the one hand with a further top flap 19 and on the other with a fastening strip 20.

The back wall 13 and the front wall 12 are integrally connected to one another via a side wall 21, there being arranged opposite that side wall 21, on the front wall 12, a further side wall 21. The side walls 21 have at the bottom dust flaps 22 which, together with the bottom flaps 14, form a bottom 23 for the folded carton 11 when the package blank 10 is assembled.

To form a top 24, there are provided first the above-mentioned top flaps 15 arranged via fold lines 16 on the front and back walls 12, 13 and gusset flaps 25 arranged at the top on the side walls 21 and the connecting strip 17.

Depending on the width b of the connecting strip 17 between the back wall 13 and the dividing wall 18, the folded carton 11 is divided quite specifically into chambers 26 and 27, the position of the dividing wall 18 after the folded carton 11 has been assembled being shown by a dot-dash line 28 in FIG. 1.

Arranged in the chambers 26 and 27—as shown by a dotted line in FIG. 1—are tube-like inner sachets 29 and 30, respectively. The inner sachets 29, 30 generally consist of paper which, in order to seal it completely, is covered with, for example, polyethylene, polyester or aluminium.

Figure 2:
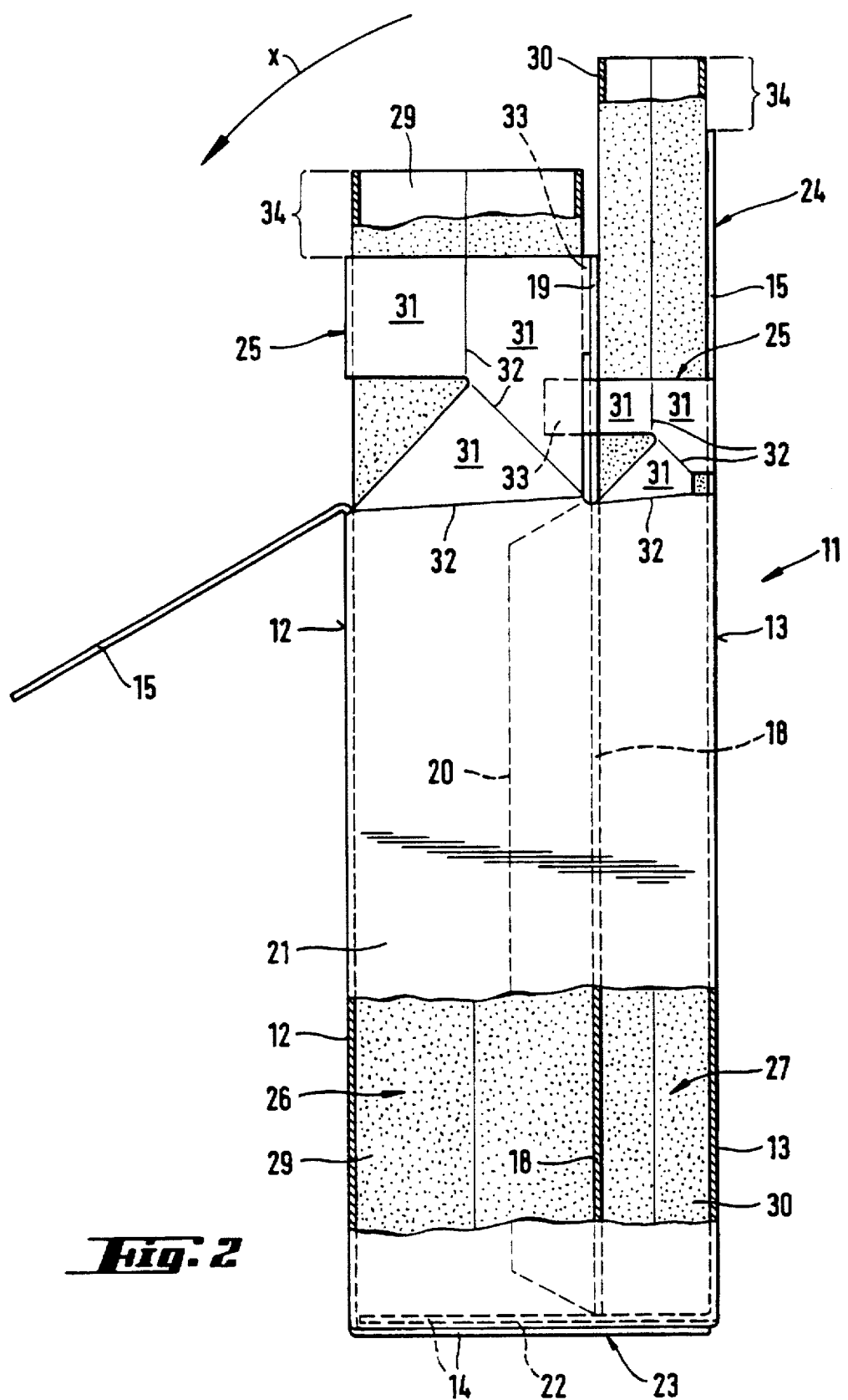
FIG. 2 is a side view of an assembled, opened folded carton corresponding to the package blank according to FIG. 1.

The function of the gusset flaps 25 can be seen clearly from the side view of the folded carton 11 shown in FIG. 2. The gusset flaps 25 are matched to the width of the individual chambers 26 and 27. They have portions 31 connected to one another by fold lines 32 in such a manner as to be movable. Those portions 31 are glued to the opposing regions of the inner sachets 29 and 30, the gusset flaps 25 additionally being connected in a fixed manner via securing regions 33 to the top flap 19 of the dividing wall 18 in the one case and to the top flap 15 of the back wall 13 in the other case.

To produce the folded carton 11 described, first of all the package blank 10 is printed and stamped from a sheet of cardboard. The package blank 10 is then joined at the places provided for glueing to form the folded carton 11. The tube-like inner sachets 29 and 30 are introduced into the folded carton 11, which is still open at the top and at the bottom, and joined to the folded carton 11 via glueing points. In that state, the folded carton 11 with the inner sachets 29, 30 glued into it can still be flattened, thus facilitating the transportation of the folded carton 11 intended for filling.

Finally, before the components of a product are introduced, the opening at the bottom of the tube-like inner sachets 29, 30 is sealed or glued and the bottom 23 of the folded carton 11 is closed.

As can be seen from FIGS. 1 and 2, when the folded carton 11 has been assembled the end regions 34 of the inner sachets 29 and 30 arranged in the chambers 26 and 27 project beyond the top flaps 15 and 19, respectively.

Figure 3:
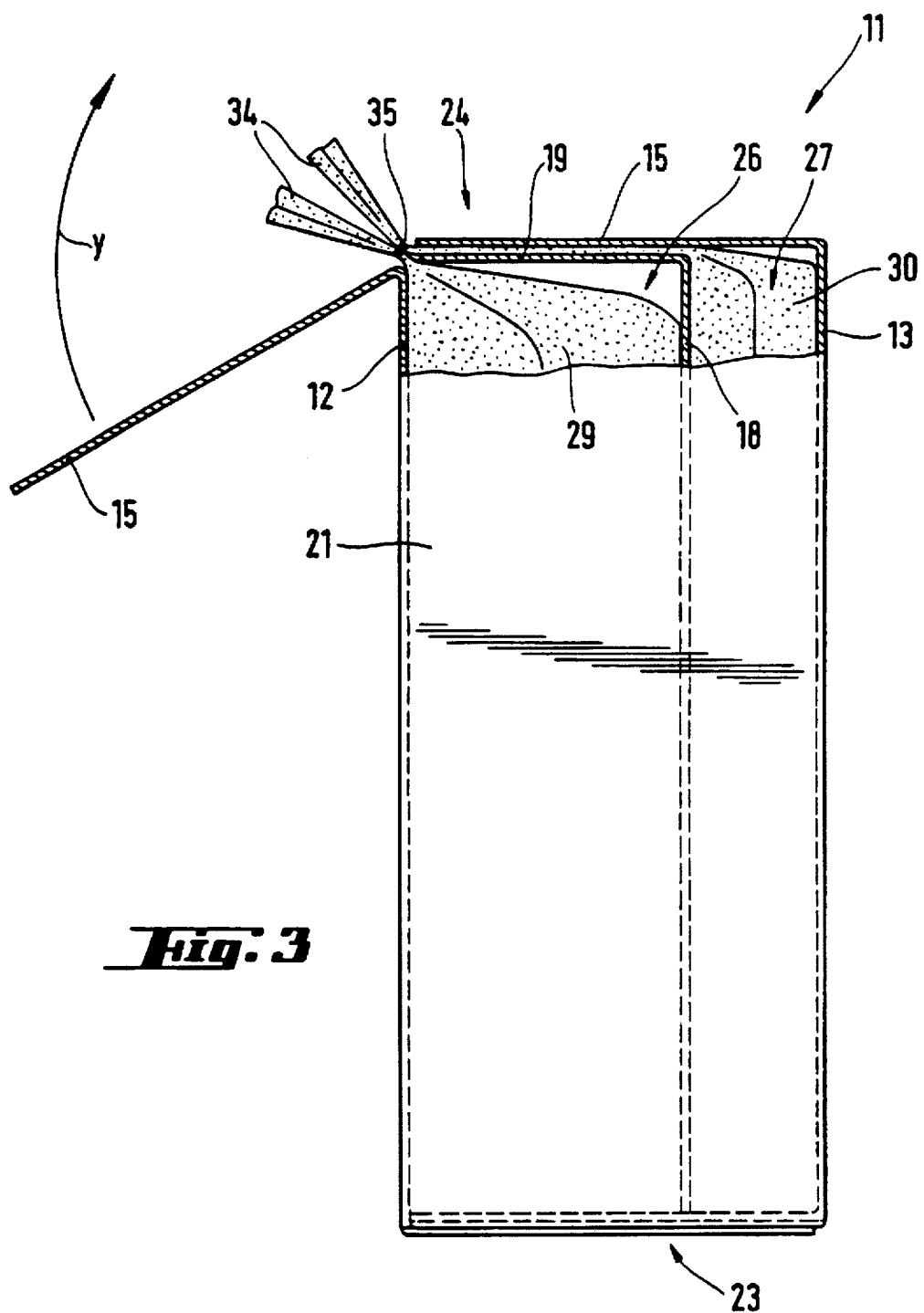
FIG. 3 is a folded carton according to FIG. 2 in a partially closed state.

FIGS. 2 and 3 show essentially the principle of the closure of the folded carton 11. When the top flap 15 of the back wall 13 and the top flap 19 of the dividing wall 18 are moved in the direction x, the inner sachets 29 and 30 are folded in neatly in the region of the fold lines 32 with the aid of the gusset flaps 25 arranged on the top flaps 15 and 19 and connected flat against the inner sachets 29 and 30. When the top flaps have reached the position shown in FIG. 3, the end regions 34 of the inner sachets 29, 30 projecting beyond the top flaps 15 and 19 can be sealed using a tool (not shown) with a common heat-sealed or glued seam 35. That ensures that the components of a product present in the inner sachets 29 and 30 are reliably sealed off. When the top flap 15 of the front wall 12 has been folded over in the opposite direction y and has been glued to the top flap 15 of the back wall 13 arranged under it, the top 24 of the folded carton 11 is completely closed. The top 24 can also be closed by inserting the top flap 15 of the front wall 12 into the top flap 15 of the back wall 13.

In order to open such a folded carton 11, the top flap 15 of the front wall 12 must be detached from the top flap 15 under it, in order to return to the state shown in FIG. 3. Then, by simply tearing off the end regions 34 by hand or cutting them off with scissors in the region between the end edges of the covering flaps 15, 19 and the heat-sealed and glued seam 35, the two inner sachets 29 and 30 arranged in the folded carton 11 can be opened simultaneously, allowing the product to be used immediately simply by emptying the folded carton 11.

Figure 4:
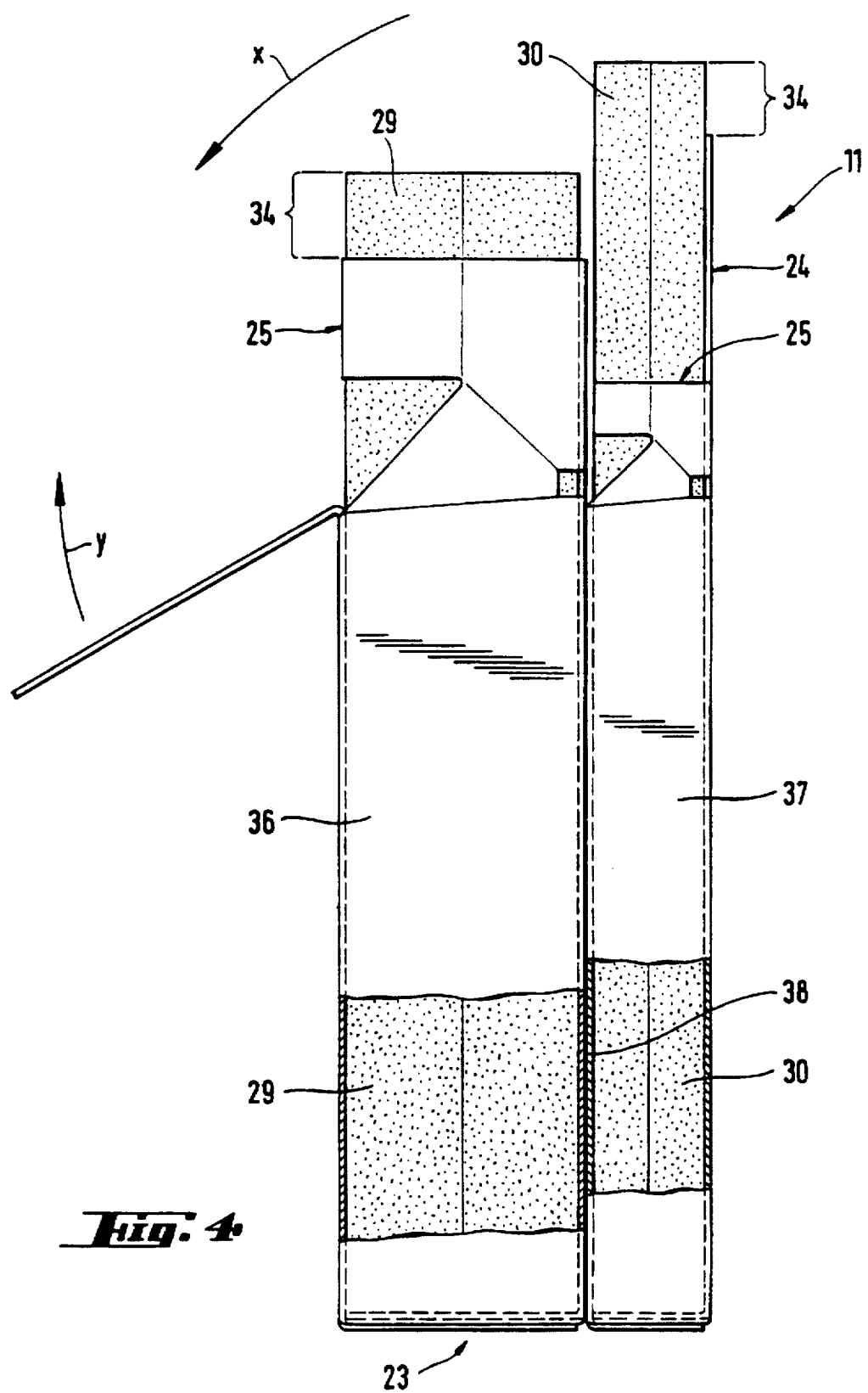
FIG. 4 is a representation according to FIG. 2 but with two separate package blanks.

FIG. 4 corresponds substantially to FIG. 2 as regards the construction of the top closure 24, but the folded carton 11 shown in FIG. 4 consists of two completely separate folded carton portions 36 and 37. The folded carton portions 36 and 37 likewise have associated inner sachets 29 and 30, respectively, the folded carton portions being glued together in the region of the opposing front and back walls to form a double dividing wall 38. The folded carton 11 thus created can in turn have a common closure as described above.

When the folded carton 11 consisting of two folded carton portions 35 and 36 is later opened, it may be advisable in certain applications to separate the individual portions of the folded carton 11 from one another again.

FIGS. 5 and 6 show an embodiment of a folded carton 11 having top flaps 39 and 40 and two dust flaps 41, only one of which can be seen. That folded carton 11 also has a dividing wall 42, shown by a dotted line, which divides the inside of the folded carton 11 into two chambers 43 and 44 in which are arranged inner sachets 45 and 46 the end regions 48 of which project out of the opening region of the folded carton 11. The end regions 48 of the inner sachets 45 and 46 which project out of the opening region of the folded carton 11 are folded together and are sealed together approximately centrally above the folded carton 11 by means of a heat-sealed or glued seam. The folded carton 11 can then be closed by folding or rolling up the end region 48 (in a manner not shown) and folding over the dust flaps 42 and the top flaps 39, 40.

On the one hand the package according to the invention is not limited to the embodiments shown, and on the other hand a combination of various closures at the top and bottom of a package is also conceivable.

In an especially simple form of the package according to the invention, the chambers for accommodating the individual components are formed by individual sachets having preferably flexible boundary walls. Each of the individual sachets is connected to another individual sachet at least along a portion of one of its boundary walls. In that manner the individual sachets cannot be detached from one another without tearing the boundary wall of at least one chamber. That ensures that the sachets are used only jointly. The individual components can only be administered from the individual sachets jointly. That is achieved by joining the end regions of the boundary walls of the individual sachets to form a common closure. In an alternative form, the chambers are provided in a single sachet having flexible boundary walls and are separated from one another by at least one flexible partition wall. In that case the boundary walls and the partition wall are joined at their end regions to form a common closure. It is also possible to join a combination of individual sachets and multi-chambered sachets to form a group.

The walls defining the chambers are preferably glued, heat-sealed, welded or otherwise permanently joined together. It is advantageous for the sachets to be in the form of standing sachets, preferably having a common base. In that way the sachet groups can also be transported and stored in an upright position.

The sachets can be made from various materials. Examples of suitable materials are coated or uncoated monofoils made from metal, preferably aluminium, plastics or paper, or laminates of at least two identical or different materials. The choice of material depends especially, however, on the individual chemical components with which the sachets are to be filled, and on the strength properties required.

What is claimed is:

1. A package for accommodating a product having at least two components, which package has at least two self-contained compartments in which the individual components of the product can be stored in such a manner that they are hermetically separated from one another, wherein the compartments are coupled together in such a manner that they can be separated from one another only by destroying at least one compartment wall, and wherein the end regions of the compartment walls are in the form of a common closure for the individual compartments such that the individual compartments can only be opened simultaneously; characterized in that the package further comprises at least one folded carton (11) having essentially a front and a back wall, side walls, bottom flaps and top flaps, inside which carton there are arranged in a fixed manner at least two inner sachets (29, 30; 45, 46), said inner sachets each are composed of a top end region (34, 48) and each of which accommodates one of the components directly and which represent the compartments for the individual components, said inner sachets are composed of a material selected from the group consisting of paper, single layered plastic film, multi-layered plastic film and other composite material, the top end regions (34; 48) of the sachets projecting out of the inside of the folded carton (11) when the top flaps are in the open position and forming said common closure (35; 49) when the inner sachets have been filled separately, and wherein the folded carton (11) has two chambers (26, 27; 43, 44), separated by a dividing wall (18; 42), in which the inner sachets are arranged.

2. A package according to claim 1, wherein the dividing wall (18, 42) divides the folded carton (11) into chambers (26, 27; 43, 44) of different sizes.

3. A package according to claim 1, wherein the front, dividing and back walls (12; 13; 18) each have an integrally arranged top flap (15, 19); the length of the top flap (15) of the back wall (13) corresponds substantially to the distance of the back wall (13) from the front wall (12) and the length of the top flap (19) of the dividing wall (18) corresponds substantially to the distance of the dividing wall (18) from the front wall (12); end regions (34) of the inner sachets (29, 30) project beyond the top flaps (15, 19) of the back and dividing walls, which flaps can be folded over in the direction (x) towards the front wall (12): the end regions (34) form a common closure (35) when the top flaps (15, 19) of the back and dividing walls (13; 18) have been folded over, and when the top flap (15) on the front wall is folded over in the opposite direction (y) the closure can be held within the contour of the folded carton (11).

4. A package according to claim 3, wherein the folded carton (11) consists of two folded carton portions (36, 37) each of which forms a chamber (43, 44) and which are joined together to form a double-thickness dividing wall (42).

5. A package according to claim 1, wherein there are arranged on both sides of the package blank (10), between the back wall (13) and the dividing wall (18); gusset flaps that can be folded in in the direction towards the top flap (15) of the front wall (12) and the inside of the folded carton (11).

6. A package according to claim 5, wherein at least portions of the inner sachets (29, 30) are secured by means of adhesive to the front, back and dividing walls (12; 13; 18), the associated top flaps (15, 19) and the gusset flaps (25).

7. A package according to claim 1, wherein, once the front wall top flap (15) has been opened, the common closure (35, 49) can be removed by cutting through the end regions (34) of the two inner sachets (29, 30) along the end edges of the top flaps (15, 19) of the back and dividing walls (13; 18).

8. A package according to claim 1, wherein the folded carton (11) is divided into chambers (26, 27; 43, 44) of different widths each of which accommodates a correspondingly dimensioned inner sachet (29, 30; 45, 46).

9. A package according to claim 1, wherein the common closure is in the form of a heat-sealed seam (35, 49).

10. A package according to claim 1, wherein the common closure is in the form of a glued seam (35, 49).

11. A package according to claim 1, wherein tube-like inner sachets (29, 30; 45, 46) made of paper are coated with polyethylene to form a hermetic seal for the product components stored therein.

12. A package according to claim 1, wherein tube-like inner sachets (29, 30; 45, 46) made of paper are coated with polyester to form a hermetic seal for the product components stored therein.

13. A package according to claim 1, wherein tube-like inner sachets (29, 30; 45, 46) made of paper are coated with aluminium to form a hermetic seal for the product components stored therein.

* * * * *